United States Patent
Barranco-Medina et al.

(10) Patent No.: US 11,085,031 B2
(45) Date of Patent: *Aug. 10, 2021

(54) THROMBIN-THROMBOMODULIN FUSION PROTEINS AS A POWERFUL ANTICOAGULANT

(71) Applicant: Saint Louis University, St. Louis, MO (US)

(72) Inventors: Sergio Barranco-Medina, Manchester, MO (US); Enrico Di Cera, Ladue, MO (US); Nicola Pozzi, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 135 days.

This patent is subject to a terminal disclaimer.

(21) Appl. No.: 16/097,485

(22) PCT Filed: Apr. 28, 2017

(86) PCT No.: PCT/US2017/030013
§ 371 (c)(1),
(2) Date: Oct. 29, 2018

(87) PCT Pub. No.: WO2017/189943
PCT Pub. Date: Nov. 2, 2017

(65) Prior Publication Data
US 2019/0153419 A1 May 23, 2019

Related U.S. Application Data

(60) Provisional application No. 62/329,001, filed on Apr. 28, 2016.

(51) Int. Cl.
*C12N 9/74* (2006.01)
*A61K 9/00* (2006.01)
*C07K 14/745* (2006.01)
*C12N 15/62* (2006.01)
*A61P 7/02* (2006.01)
*A61K 38/36* (2006.01)
*A61K 38/48* (2006.01)
*A61K 45/06* (2006.01)
*A61K 38/00* (2006.01)

(52) U.S. Cl.
CPC .......... *C12N 9/6429* (2013.01); *A61K 9/0019* (2013.01); *A61K 38/366* (2013.01); *A61K 38/4833* (2013.01); *A61K 45/06* (2013.01); *A61P 7/02* (2018.01); *C07K 14/7455* (2013.01); *C12N 15/62* (2013.01); *C12Y 304/21005* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,679,639 A | * | 10/1997 | Griffin | C07K 14/755 514/13.7 |
| 5,968,751 A | * | 10/1999 | Griffin | C12N 9/647 435/7.1 |
| 7,622,122 B2 | | 11/2009 | Light et al. | |
| 8,940,297 B2 | * | 1/2015 | Di Cera | A61P 7/02 424/94.64 |
| 2003/0186883 A1 | * | 10/2003 | Light | C07K 14/7455 514/14.9 |
| 2010/0159512 A1 | | 6/2010 | Osther | |
| 2012/0164129 A1 | | 6/2012 | Di Cera et al. | |
| 2018/0127735 A1 | * | 5/2018 | Barranco-Medina | C07K 14/7455 |

FOREIGN PATENT DOCUMENTS

WO 2016176440 A2 11/2016

OTHER PUBLICATIONS

Adams et al., Molecular basis of thrombomodulin activation of slow thrombin; Journal of Thrombosis and Haemostasis, vol. 7, pp. 1688-1695.
Cantwell et al., Rational Design of a Potent Anticoagulant Thrombin; The Journal of Biological Chemistry, vol. 275, No. 51, 2000, pp. 39827-39830.
Chen et al., Fusion Protein Linkers: Property, Design and Functionality; Adv. Drug Deliv. Rev., 2013, vol. 65, No. 10, pp. 1357-1369.
Dang et al., Chromogenic substrates selective for activated protein C. Blood, 1007, vol. 89, No. 6, pp. 2220-2222.
Eikelboom et al., Idarucizumab, The Antidote for Reversal of Dabigatran, 12 pages.
Marino et al., Engineering Thrombin for Selective Specificity toward Protein C and PAR1; The Journal of Biological Chemistry, 2010, vol. 285, No. 25, pp. 19145-19152.

* cited by examiner

*Primary Examiner* — Hope A Robinson
(74) *Attorney, Agent, or Firm* — Stinson LLP

(57) ABSTRACT

Compositions and methods for regulating the blood coagulation pathway are disclosed. More particularly, the present disclosure relates to thrombin-thrombomodulin fusion proteins and their use as blood anticoagulants and for treating sepsis.

5 Claims, 1 Drawing Sheet
Specification includes a Sequence Listing.

THROMBIN-THROMBOMODULIN FUSION PROTEINS AS A POWERFUL ANTICOAGULANT

CROSS-REFERENCE TO RELATED APPLICATIONS

This application is a U.S. National Phase Application of PCT/US2017/030013 (published as WO 2017/189943), filed on Apr. 28, 2017, which claims priority to U.S. Provisional Patent Application Ser. No. 62/329,001, filed on Apr. 28, 2016, the disclosures of which are hereby incorporated by reference in their entireties.

STATEMENT REGARDING FEDERALLY SPONSORED RESEARCH OR DEVELOPMENT

This invention was made with government support under HL49413, HL73813 and HL112303 awarded by the National Heart Lung and Blood Institute. The Government has certain rights in the invention.

STATEMENT IN SUPPORT FOR FILING A SEQUENCE LISTING

A paper copy of the Sequence Listing and a computer readable form of the Sequence Listing containing the file named "SLU16004_US_ST25.txt", which is 47,996 bytes in size (as measured in MICROSOFT WINDOWS® EXPLORER), are provided herein and are herein incorporated by reference. This Sequence Listing consists of SEQ ID NOs:1-25.

BACKGROUND OF THE DISCLOSURE

The present disclosure relates generally to compositions and methods for regulating the blood coagulation pathway. More particularly, the present disclosure relates to the use of thrombin-thrombomodulin fusion proteins as blood anticoagulants. Also disclosed is the use of thrombin-thrombomodulin fusion proteins to treat sepsis.

Thrombin (coagulation factor II, EC 3.4.21.5) is a serine protease involved in the coagulation cascade. Thrombin is formed by the proteolytic cleavage of prothrombin. Thrombin promotes coagulation by converting factor XI to factor XIa, factor VIII to factor VIIIa, factor V to factor Va, factor XIII to factor XIIIa, and soluble fibrinogen into insoluble strands of fibrin. The production of thrombin in vivo occurs through a series of intermediate forms, including prothrombin, prethrombin-1, and prethrombin-2. Each step involves a highly regulated cleavage of the precursor form of thrombin, until mature thrombin is produced. Mature thrombin is formed of two polypeptide chains, the A chain and the B chain, with a disulfide bond between the A and the B chain, and can be produced by cleavage of prethrombin-2 at a specific site.

Thrombin also functions as one of the key components in the homeostasis of the coagulation cascade. The specific binding of fibrinogen and PAR-1 to the exosite-1 of thrombin leads to the conversion of fibrinogen to fibrin, platelet activation and clot formation. The procoagulant activity of thrombin can be switched to an anticoagulant activity when the very same exosite-1 is bound to the cofactor thrombomodulin (TM). Thrombomodulin is an integral membrane protein expressed on the surface of endothelial cells and serves as a cofactor for thrombin.

The binding of thrombin and thrombomodulin results in the activation of protein C by 1500-fold and activation of protein C promotes the inactivation of the coagulation cascade. Specifically, activated protein C then degrades clotting factors Va and VIIIa. Once in circulation, activated protein C shuts down the coagulation cascade by degrading factor Va and VIIIa and, in turn, ends thrombin generation and prevents further clotting. Thus, the formation of the thrombin-thrombomodulin complex enables the most powerful enzymatic anticoagulant system that exists in vivo.

Congenital or acquired protein C and thrombin mutations/deficiencies are established risk factors of thrombosis. Formation of thrombus in a blood vessel can reduce blood flow to a tissue, resulting in hypoxia and accumulation of metabolic products. A larger thrombus causing a much greater obstruction to the blood flow may result in anoxia, the complete deprivation of oxygen and infarction, tissue death. A clot that forms to prevent bleeding can break free and travel around the body, which can result in reduced blood flow to a tissue or tissue death.

The current list of anticoagulant drugs available to treat coagulation disorders targets different key factors of the coagulation cascade, mostly inhibiting procoagulant factors. None of those has successfully achieved a stimulation of the anticoagulant pathway through activation of protein C, however.

Accordingly, there exists a need to develop anticoagulant/antithrombotic agents and uses of anticoagulant/antithrombotic agents as blood anticoagulants.

BRIEF DESCRIPTION OF THE DISCLOSURE

The present disclosure is generally directed to compositions and methods for regulating the blood coagulation pathway. More particularly, particularly, the present disclosure relates to the use of thrombin-thrombomodulin fusion proteins as blood anticoagulants. Also disclosed are uses of thrombin-thrombomodulin fusion proteins to treat sepsis.

In one aspect, the present disclosure is directed to a thrombin-thrombomodulin fusion protein comprising a thrombin domain and a thrombomodulin domain.

In one aspect, the present disclosure is directed to composition comprising a thrombin domain, a linker domain, wherein the linker domain ranges from about 20 amino acid residues to about 50 amino acid residues; and a thrombomodulin domain.

In another aspect, the present disclosure is directed to a method for treating thrombosis in an individual in need thereof. The method comprises: administering to an individual in need thereof a composition comprising a thrombin-thrombomodulin fusion protein, wherein the individual has or is suspected of having a blood clot.

In another aspect, the present disclosure is directed to a method for treating sepsis in an individual in need thereof. The method comprises administering to an individual in need thereof a composition comprising a thrombin-thrombomodulin fusion protein, wherein the individual has or is suspected of having sepsis.

In accordance with the present disclosure, uses of thrombin-thrombomodulin fusion proteins have been discovered that allow for use as blood anticoagulants. The compositions and methods of the present disclosure have a broad and significant impact, as they provide new agents that function as powerful anticoagulants and treatments for sepsis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein.

Figures 1A, 1B, 1C:
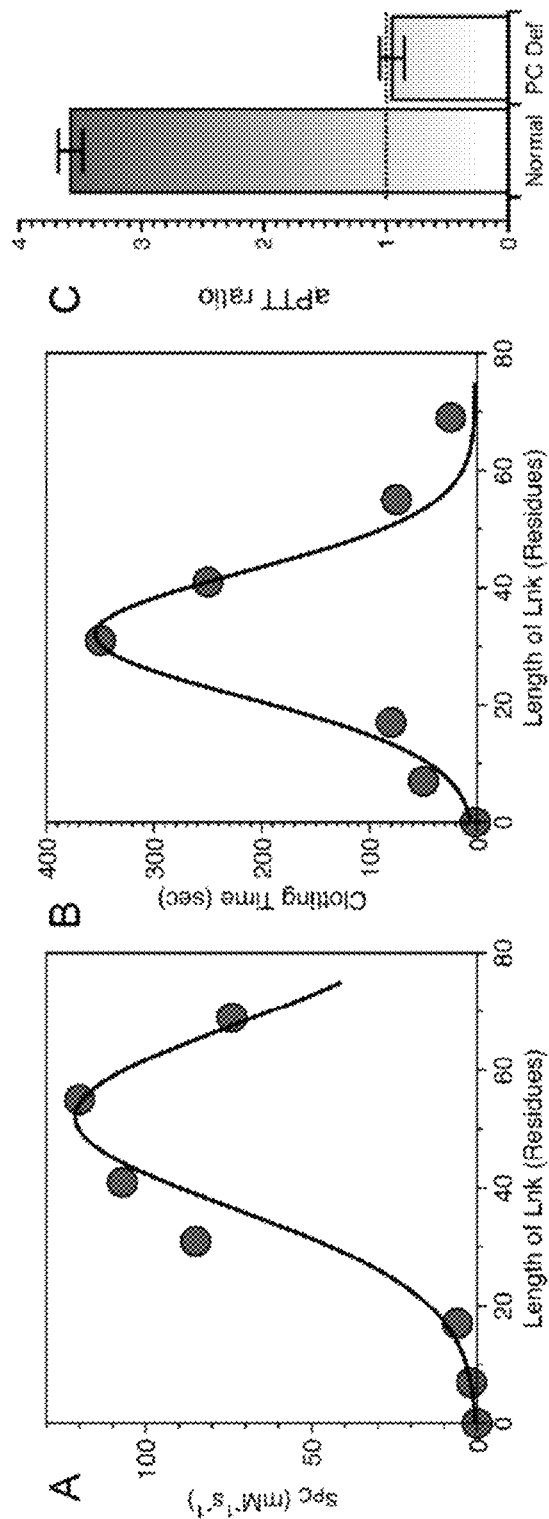
FIG. 1A is a graph depicting the effect of linker domain (lnk) length on the rate of protein C activation.
FIG. 1B is a graph depicting the effect of linker domain (lnk) length on fibrinogen cleavage.
FIG. 1C is a graph depicting aPTT measurement following addition of a thrombin-linker-thrombomodulin fusion protein having a WE thrombin domain and linker domain of 31 amino acid residues (L31) to normal plasma and protein C deficient (PC Def) plasma.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed herein are thrombin-thrombomodulin fusion proteins useful to treat thrombosis and sepsis. The thrombin-thrombomodulin fusion proteins of the present disclosure exploit the exclusive role of thrombomodulin to convert thrombin into a potent anticoagulant. Administration of the thrombin-thrombomodulin fusion proteins of the present disclosure enables on-demand generation of activated protein C (aPC) in the body by taking advantage of the natural pool of protein C to generate, in the body, aPC. The thrombin-thrombomodulin fusion proteins of the present disclosure also enable the activation of protein C without the need for endogenous or co-administration of thrombomodulin. Activating protein C in vivo has been demonstrated in animal models of stroke using other protein C activating compounds.

Thrombin-Thrombomodulin Fusion Proteins

In one aspect, the present disclosure is directed to thrombin-thrombomodulin fusion proteins. The thrombin-thrombomodulin fusion protein includes a thrombin domain and a thrombomodulin domain. The thrombin-thrombomodulin fusion proteins can further include a linker domain.

The thrombin domain can be a full-length thrombin polypeptide, a preprothrombin polypeptide, a prothrombin polypeptide, a prethrombin 1 polypeptide, a prethrombin 2 polypeptide, a thrombin A chain, a thrombin B chain, and combinations thereof. A particularly suitable thrombin domain is prethrombin 1. The preprothrombin amino acid sequence (from UniProtKB database accession number P00734) represents the full thrombin polypeptide as it is initially expressed. Amino acids 1-24 of SEQ ID NO:1 are the signal peptide, and amino acids 25-43 of SEQ ID NO:1 are a propeptide that is removed to form prothrombin (amino acids 44-622 of SEQ ID NO:1). Amino acids 44-198 of SEQ ID NO:1 are removed when prothrombin is cleaved by thrombin to form prethrombin-1 (amino acids 199-622 of SEQ ID NO:1). Amino acids 199-327 of SEQ ID NO: 1 are removed when prethrombin-1 is cleaved by activated factor X (Xa) (or other enzymes) to form prethrombin-2 (amino acids 328-622 of SEQ ID NO:1). Finally, prethrombin-2 is cleaved by Xa to form the A chain (also called the light chain) (amino acids 328-363 of SEQ ID NO:1), and the B chain (also called the heavy chain) (amino acids 364-622 of SEQ ID NO:1) of mature thrombin.

A suitable thrombin domain can have a nucleotide sequence of SEQ ID NO:2. A suitable thrombin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:2. Another suitable thrombin domain can have a nucleotide sequence of SEQ ID NO:4. A suitable thrombin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:4. SEQ ID NO:4 includes an ecarin cleavage site encoded by the nucleotides located at positions 493-501 of SEQ ID NO:4.

Percent identity of two sequences can be determined by aligning the sequences for optimal comparison. For example, gaps can be introduced in the sequence of a first nucleic acid sequence for optimal alignment with the second nucleic acid sequence. The same can be done for optimal alignment of amino acid sequences. The nucleotides or amino acid residues at corresponding positions are then compared. When a position in the first sequence is occupied by the same nucleotide or amino acid as at the corresponding position in the second sequence, the nucleic acids or amino acids are identical at that position. The percent identity between the two sequences is a function of the number of identical nucleotides or amino acids shared by the sequences. Hence, percent identity=[number of identical nucleotides/total number of overlapping positions]×100 or percent identity=[number of identical amino acids/total number of overlapping positions]×100. The percentage of sequence identity can be calculated according to this formula by comparing two optimally aligned sequences being compared, determining the number of positions at which the identical nucleic acid or amino acid occurs in both sequences to yield the number of matched positions (the "number of identical positions" in the formula above), dividing the number of matched positions by the total number of positions being compared (the "total number of overlapping positions" in the formula above), and multiplying the result by 100 to yield the percent sequence identity. In this comparison, the sequences can be the same length or may be different in length. Optimal alignment of sequences for determining a comparison window can be conducted by the local homology algorithm of Smith and Waterman (1981), by the homology alignment algorithm of Needleman and Wunsh (1972), by the search for similarity via the method of Pearson and Lipman (1988), by computerized implementations of these algorithms (GAP, BESTFIT, FASTA and TFASTA in the Wisconsin Genetics Software Package Release 7.0, Genetic Computer Group, 575, Science Drive, Madison, Wis.), or by inspection.

A suitable thrombin domain can have an amino acid sequence of SEQ ID NO:3. A suitable thrombin domain can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:3. Another suitable thrombin domain can have an amino acid sequence of SEQ ID NO:5. A suitable thrombin domain can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:5. SEQ ID NO:5 includes an ecarin cleavage site located at amino acid residues 165-167 of SEQ ID NO:5.

The thrombin domain can further include a thrombin variant. The double thrombin mutant referred to as W215A/E217A thrombin (or "WE-thrombin variant") is constructed by combining the two single mutations W215A and E217A in the human thrombin molecule (as described in Cantwell and Di Cera, J. Biol. Chem. 2000; 275:39827-39830, which is incorporated by reference in its entirety). W215A and E217A refer to amino acid residue positions in the thrombin amino acid residue sequence using the position numbers as described in Bode et al. (EMBO J 1989; 8(11):3467-3475, which is incorporated by reference in its entirety) that corresponds to amino acids 590 and 592 of SEQ ID NO: 1, respectively. Another suitable thrombin variant can be a WE thrombin variant of SEQ ID NO:3 in which the tryptophan (single amino acid letter code W) residue at 430 of SEQ ID NO:3 is substituted with an alanine ($W_{430} \rightarrow A_{430}$) and the glutamic acid (single amino acid letter code E) residue at 432 is substituted with an alanine ($E_{432} \rightarrow A_{432}$). Another suitable thrombin variant can be a WE thrombin variant of SEQ ID NO:5 in which the tryptophan (single amino acid letter code W) residue at 430 of SEQ ID NO:5 is substituted with an alanine ($W_{430} \rightarrow A_{430}$) and the glutamic acid (single amino acid letter code E) residue at 432 is substituted with an alanine ($E_{432} \rightarrow A_{432}$). The human thrombin referred to as the E-WE-thrombin variant is a WE-thrombin variant that has been produced in *E. coli* (US Patent Application Publication 2012/0164129 A1). WE thrombin variants have enhanced protein C activating properties, and reduced fibrinogen-cleaving activity, making them highly anticoagulant thrombins. Other suitable thrombin variants are described in a large number of thrombin polypeptide variants have been characterized in Marino et al., (J. Biol. Chem. 2010; 285(25):19145-19152, which is incorporated by reference in its entirety. The activity of thrombin variants can be analyzed using variety of in vitro assays including, for example, cleavage of prothrombin, cleavage of fibrinogen, and cleavage of fibrin; the activation of protein C, and the interaction with PAR-1 (Cantwell and Di Cera, J. Biol. Chem. 2000; 275(51): 39827-39830). Anticoagulant effects of thrombin variants can also be determined using in vivo assays in experimental animals.

The thrombomodulin domain can be a full-length thrombomodulin protein. A particularly suitable thrombomodulin domain can be thrombomodulin's epidermal growth factor-like domains 456 (TM456). A particularly suitable thrombomodulin domain can have a nucleotide sequence of SEQ ID NO:6 encoding thrombomodulin's epidermal growth factor-like domains 456 (TM456). A suitable thrombomodulin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:6.

A particularly suitable thrombomodulin domain can be thrombomodulin's epidermal growth factor-like domains 456 (TM456) having an amino acid sequence of SEQ ID NO:7. A suitable thrombomodulin domain using thrombomodulins epidermal growth factor-like domains 456 (TM456) can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:7.

Another suitable thrombomodulin domain can be thrombomodulin's epidermal growth factor-like domains 456 (TM456) as encoded by SEQ ID NO:8. A suitable thrombomodulin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:8.

Another suitable thrombomodulin domain can be thrombomodulin's epidermal growth factor-like domains 456 (TM456) having an amino acid sequence of SEQ ID NO:9. A suitable thrombomodulin domain using thrombomodulins epidermal growth factor-like domains 456 (TM456) can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:9.

The thrombin-thrombomodulin fusion protein can further include a linker. A linker functions to couple the thrombin domain to the thrombomodulin domain and to provide distance between the thrombin domain and the thrombomodulin domain. Suitable linkers include, for example, peptide linkers and chemical linkers. Suitable peptide linkers can range from about 20 amino acid residues to about 50 amino acid residues. Particularly suitable linker domains can range from about 30 amino acid residues to about 41 amino acid residues. Particularly suitable linkers are flexible linkers enriched in small amino acids and polar amino acids such as, for example, glycine and serine. Exemplary peptide linkers are shown in Table 1.

TABLE 1

Linker Sequences.

| Linker Name | Amino Acid Sequence | SEQ ID NO: |
|---|---|---|
| L7 | GGGGGGG | 10 |
| L17 | GGGSSSAGGGSSSGGGG | 11 |
| L31 | GGGSSSAGGGSSSGGGGSSSAGGGSSSGGGG | 12 |
| L41 | GGGSSSAGGGSSSGGGGSSSAGGGSSSGGGG ASSSGSAGSS | 13 |
| L55 | GGGSSSAGGGSSSGGGGSSSAGGGSSSGGGG ASSSGSAGSSGGGGASSSGSAGSS | 14 |
| L69 | GGGSSSAGGGSSSGGGGSSSAGGGSSSGGGG SSSAGGGSSSGGGGSSSAGGGSSSGGGGASS SGSAGSS | 15 |

The thrombin-thrombomodulin fusion protein can further include a tag. Suitable tags can be purification tags and labels. Suitable purification tags can be histidine tags and HPC4 tags. A particularly suitable HPC4 tag is an HPC4 epitope tag having the amino acid sequence LEDQVDPR-LIDGK (SEQ ID NO:16).

The thrombin-thrombomodulin fusion protein can further include at least one protease cleavage site. Protease cleavage sites can be incorporated into the thrombin-thrombomodulin fusion protein for purification or other purposes. A particularly suitable thrombin cleavage site is an auto-lytic thrombin cleavage site having the structure of P4-P3-Pro-Arg-P1'-P2' wherein P4 and P3 are hydrophobic amino acids and P1' and P2' are non acidic amino acids. Particularly suitable thrombin cleavage sites include SEQ ID NO:24 and SEQ ID NO:25. The thrombin cleavage site is inserted by substituting at least one amino acid located at residues 360 to 365 with reference to SEQ ID NO:1. For example, the glycine amino acid at position 362 of SEQ ID NO:1 can be replaced with a proline. The isoleucine at position 364 of SEQ ID NO:1 can be replaced with a glycine. A particularly suitable protease cleavage site can be at least one ecarin cleavage site. A second ecarin cleavage site is not necessary, but slows down processing to alpha thrombin. Ecarin is a snake venom-derived protease isolated from *Echis carinate*. The cleavage site specifically recognized by ecarin is arginine-isoleucine.

The thrombin-thrombomodulin fusion protein can contain signal peptides or lack them, depending on whether it is desirable for the thrombin-thrombomodulin fusion protein to be exported from the host cell cytoplasm into the periplasm, or to be retained in the cytoplasm, respectively.

The thrombin-thrombomodulin fusion protein can further be glycosylated or unglycosylated.

A particularly suitable thrombin-thrombomodulin fusion protein is encoded by SEQ ID NO:17. Other particularly suitable thrombin-thrombomodulin fusion proteins can have nucleic acid sequence at least 80%, at least 85%, at least 90%, at least 91%, at least 92%, at least 93%, at least 94%, at least 95%, at least 96%, at least 97%, at least 98%, or at least 99% identical to SEQ ID NO:17. A particularly suitable thrombin-thrombomodulin fusion protein has an amino acid sequence of SEQ ID NO:18. Other particularly suitable thrombin-thrombomodulin fusion proteins can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:18. The polypeptide of SEQ ID NO:18 can be treated with ecarin to remove amino acid residues 1-167 to form the final product representing the "active" thrombin-thrombomodulin fusion protein containing the thrombin domain and the thrombomodulin domain. SEQ ID NO:19 is a particularly suitable active thrombin-thrombomodulin fusion protein.

Another particularly suitable thrombin-thrombomodulin fusion protein is encoded by a nucleic acid sequence of SEQ ID NO:20. SEQ ID NO:20 encodes a thrombin-thrombomodulin fusion protein that further includes the WE thrombin double mutation described herein. In particular, SEQ ID NO:20 contains the codon GCG at nucleotides 1288-1290 to encode an alanine and a codon GCA at nucleotides 1294-1296 to encode an alanine. Other particularly suitable thrombin-thrombomodulin fusion proteins can have nucleic acid sequence at least 80%, at least 85%, at least 90%, at least 91%, at least 92%, at least 93%, at least 94%, at least 95%, at least 96%, at least 97%, at least 98%, or at least 99% identical to SEQ ID NO:20, but which includes the WE thrombin double mutation (codon GCG at nucleotides 1288-1290 to encode an alanine and a codon GCA at nucleotides 1294-1296 to encode an alanine).

Another particularly suitable thrombin-thrombomodulin fusion protein includes the amino acid sequence of SEQ ID NO:21. SEQ ID NO:21 represents an example of a thrombin-thrombomodulin fusion protein that further includes the WE thrombin double mutation described herein. The double mutation results from a substitution of tryptophan (single letter amino acid code W) at residue 429 of SEQ ID NO:21 to an alanine (single letter amino acid code W) and a substitution of glutamic acid (single letter amino acid code E) at residue 431 of SEQ ID NO:21 to an alanine. Other particularly suitable thrombin-thrombomodulin fusion proteins can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:21, but which includes the WE thrombin double mutation (W to A substitution and E to A substitution as described herein).

The polypeptide of SEQ ID NO:21 can be treated with ecarin to remove amino acid residues 1-167 to form the final product representing the "active" thrombin-thrombomodulin fusion protein containing the thrombin domain and the thrombomodulin domain SEQ ID NO:22 is a particularly suitable active thrombin-thrombomodulin fusion protein that includes the WE thrombin double mutation (W to A substitution at residue 262 of SEQ ID NO:22 and E to A substitution at residue 264 of SEQ ID NO:22). Other particularly suitable thrombin-thrombomodulin fusion proteins can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:22, including the WE thrombin double mutation (W to A substitution and E to A substitution as described herein).

The composition can further include carriers and excipients. Suitable carriers include pharmaceutically acceptable carriers. Suitable excipients include pharmaceutically acceptable excipients. Particularly suitable carriers include sterile isotonic solutions. As used herein, the term "pharmaceutically acceptable carrier" refers to a carrier or a diluent that does not cause significant irritation to an organism and does not abrogate the biological activity and properties of the composition. Examples of carriers include, for example, saline solutions, calcium chloride solutions, propylene glycol, emulsions and mixtures of organic solvents with water. As used herein, the term "excipient" refers to an inert substance added to a composition to further facilitate administration of the composition. Examples of excipients include, for example, calcium carbonate, calcium phosphate, various sugars and types of starch, cellulose derivatives, gelatin, vegetable oils and polyethylene glycols. Formulations and administration of the compositions of the present disclosure can be found in "Remington's Pharmaceutical Sciences," Mack Publishing Co., Easton, Pa., latest edition.

For injection, the thrombin-thrombomodulin fusion proteins can be formulated in aqueous solutions, preferably in physiologically compatible buffers such as Hank's solution, Ringer's solution, or physiological saline buffer with or without organic solvents such as propylene glycol, polyethylene glycol and with or without dextrose.

Suitable routes of administration include, for example, parenteral, such as subcutaneous injection (S.C.), intravenous injection (I.V.) and intramuscular injection (I.M.) depending of the formulation, release time. Administration can include bolus injection and infusion.

Methods for Preparing Thrombin-Thrombomodulin Fusion Proteins

Thrombin-thrombomodulin fusion proteins, thrombin domains, linker domains, and thrombomodulin domains can be prepared by incorporating a cDNA fragment encoding the thrombin-thrombomodulin fusion proteins, the thrombin domains, the linker domains, and/or the thrombomodulin domains into an expression vector, transforming suitable microorganism or animal cells with the resulting expression vector, and culturing the transformed microorganism or animal cells to produce the thrombin-thrombomodulin fusion proteins, the thrombin domains, the linker domains, and the thrombomodulin domains. For production of the thrombin domains, the linker domains, and/or the thrombomodulin domains, a peptide synthesizer can also be used.

Secretion signal sequences for secretion in microorganism or animal cell expression cultures can be included in a nucleic acid encoding the thrombin-thrombomodulin fusion proteins, the thrombin domains, the linker domains, and/or the thrombomodulin domains of the present disclosure so that the thrombin-thrombomodulin fusion proteins, the thrombin domains, the linker domains, and/or the thrombomodulin domains can be expressed and secreted into a culture medium. Suitable signal sequences include, for example, pel B signal; a factor signal; immunoglobulin signal SG-1, C25 signal, and the like. A particularly suitable secretion signal sequence is a factor V secretion peptide.

Sequences for tags can be included in a nucleic acid encoding the thrombin-thrombomodulin fusion proteins, the thrombin domains, the linker domains, and/or the thrombomodulin domains of the present disclosure. Suitable tags can be purification tags and labels. Suitable purification tags can be histidine tags and HPC4 tags.

Sequences for protease cleavage sites can be included in a nucleic acid encoding the thrombin-thrombomodulin fusion proteins, the thrombin domains, the linker domains, and/or the thrombomodulin domains of the present disclosure. A particularly suitable protease cleavage site can be a cleavage site specific for cleavage by ecarin as described herein.

A variety of animal cells can be used as a host cell as described herein. A host cell can be transformed by any known methods including, for example, a calcium phosphate method, a DEAE dextran method, precipitation with e.g. lipofectin, fusion of protoplast with polyethylene glycol, electroporation, biolistic, and the like. A particularly suitable method for transfection is LIPOFECTAMINE® 3000.

The activity of the thrombin-thrombomodulin fusion proteins can be analyzed using methods known to those skilled in the art such as, for example, partial thromboplastin time (PTT) and activated partial thromboplastin time (aPTT). The activity of the thrombin-thrombomodulin fusion proteins can be analyzed by measuring protein C activity in the presence of the thrombin-thrombomodulin fusion proteins as compared to appropriate controls such as, for example, against thrombin, against thrombomodulin, against a no thrombin control, against a no thrombomodulin control. In one embodiment, the method includes incubating a plasma sample with a thrombin-thrombomodulin fusion protein in a first reaction mixture; adding a substrate of activated protein C to the first reaction mixture to form a second reaction mixture; and analyzing the second reaction mixture.

Suitable protein C substrates are known to those skilled in the art. Particularly suitable protein C substrates can be, for example, SaPC-21 (commercially available from ANIARA, West Chester, Ohio), SPECTROZYME® PCa (commercially available Sekisui Diagnostics, Samford, Conn.), a chromogenic substrate H-D-Asp-Arg-Arg-p-nitroanilide (DRR) (described in Pozzi et al., Blood 2012; 120(3):664-670), 52366 (pyroGlu-Pro-Arg-p-nitroanilide), 52266 (H-D-Val-Leu-Arg-p-nitroanilide), BIOPHEN CS-21(66), Boc-Leu-Ser-Thr-Arg-7-amido-4-methylcoumarin (SEQ ID NO:23) (commercially available from SIGMA-ALDRICH, St. Louis, Mo.). Other suitable protein C substrates are described in Dang and Di Cera (Blood 1997; 89(6):2220-2222), which is incorporated herein by reference in its entirety.

An aliquot of the first reaction mixture can be collected and added to a substrate of activated protein C to form a second reaction mixture; and analyzing the second reaction mixture.

A particularly suitable amount of the thrombin-thrombomodulin fusion protein is about 0.1 nM. A particularly suitable amount of a protein C is about 100 nM. A particularly suitable amount of chromogenic substrate is about 50 µM.

The thrombin-thrombomodulin fusion protein can also be analyzed by adding calcium to the first reaction mixture or to the second reaction mixture. A particularly suitable amount of calcium (as calcium chloride) is about 5 mM.

Any suitable method for analyzing the second reaction mixture can be used. Suitable methods can be, for example, measuring absorbance.

A suitable plasma sample can be a human plasma sample. A particularly suitable plasma sample is a citrated plasma sample. Other suitable plasma samples can be from animals such as, for example, primates, bovine, equine, mice, rats, rabbits, dogs, and cats.

Activity of the thrombin-thrombomodulin fusion proteins can also be analyzed by contacting a plasma sample with a thrombin-thrombomodulin fusion protein and a phosphatide reagent to form a first reaction mixture; adding calcium to the first reaction mixture to form a second reaction mixture; and analyzing the second reaction mixture.

Any suitable method for analyzing the second reaction mixture can be used. Suitable methods can be, for example, measuring clotting time of the second reaction mixture, spectrophotometrically measuring the turbidity of the second reaction mixture, and combinations thereof.

A suitable plasma sample can be a human plasma sample. A particularly suitable plasma sample is a citrated plasma sample. Other suitable plasma samples are animal plasma samples.

Suitable phosphatide reagents can be, for example, ACTIN® and DADE® ACTIN® (commercially available from Siemens Healthcare Diagnostics, Inc., Tarrytown, N.Y.).

The thrombin-thrombomodulin fusion proteins can also be analyzed in kinetic experiments toward procoagulant substrates such as, for example, fibrinogen and PAR-1.

Particularly suitable thrombin-thrombomodulin fusion proteins have a protein C activation ranging from about 80 $mM^{-1}sec^{-1}$ to about 110 $mM^{-1}sec^{-1}$. Particularly suitable thrombin-linker-thrombomodulin fusion proteins have a specificity of cleavage ($k_{cat}/K_m$) for fibrinogen ranging from about 0.25 $\mu M^{-1}sec^{-1}$ to about 0.61 $\mu M^{-1}sec^{-1}$. Particularly suitable thrombin-thrombomodulin fusion proteins have a specificity of cleavage ($k_{cat}/K_m$) for PAR-1 ranging from about 0.3 $\mu M^{-1}sec^{-1}$ to about 1.1 $\mu M^{-1}sec^{-1}$. In a thrombin-thrombomodulin fusion protein having a WE thrombin domain and a 31 amino acid residue linker, the protein C activation can be about 0.69 $mM^{-1}sec^-$, the specificity of cleavage of fibrinogen can be about 2.3E-4 $\mu M^{-1}sec^{-1}$, and the specificity of cleavage of PAR-1 can be about 6.3E-4 $\mu M^{-1}sec^{-1}$.

Particularly suitable thrombin-thrombomodulin fusion proteins exhibit a prolonged clotting time up to 50-fold.

Methods for Treating Thrombosis in an Individual in Need Thereof using Thrombin-Thrombomodulin Fusion Proteins In another aspect, the present disclosure is directed to a method of treating thrombosis in an individual in need thereof. The method includes administering a composition comprising a thrombin-thrombomodulin fusion protein to an individual in need thereof, wherein the individual has or is suspected of having a blood clot.

Particularly suitable thrombin-thrombomodulin fusion proteins are described herein.

As used herein, "individual in need thereof" refers to an individual susceptible to or at risk of a specified disease, disorder, or condition. More particularly, in the present disclosure the methods of treating thrombosis can be used with an individual or subset of individuals who have, are susceptible to, and at elevated risk for experiencing thrombosis (blood clots). Particularly suitable individuals in need thereof include those having or suspected of having deep vein thrombosis, portal vein thrombosis, renal vein thrombosis, jugular vein thrombosis, Budd-Chiari Syndrome, Paget-Schoetter disease, cerebral venous sinus thrombosis, arterial thrombosis, stroke, myocardial infarction, abnormal blood flow due to venous stasis following heart failure, abnormal blood flow due to sedentary behavior, atrial fibrillation, cancer, surgery, and embolism.

The method can further include administering an antidote to the individual in need thereof. An antidote can be administered to the individual to reduce or block the activity of the thrombin-thrombomodulin fusion protein.

Methods for Treating Sepsis in an Individual in Need Thereof using Thrombin-Thrombomodulin Fusion Proteins In another aspect, the present disclosure is directed to a method for treating sepsis in an individual in need thereof. The method includes administering a composition comprising a thrombin-thrombomodulin fusion protein to an individual in need thereof.

As used herein, "individual in need thereof" refers to an individual susceptible to or at risk of a specified disease, disorder, or condition. More particularly, in the present disclosure the methods of treating thrombosis can be used with an individual or subset of individuals who have, are susceptible to, and at elevated risk for experiencing sepsis, including severe sepsis and septic shock. As known to those skilled in the art, a diagnosis of sepsis is made when an individual exhibits at least two sepsis symptoms, plus a probable or confirmed infection. Sepsis symptoms include: body temperature above 101° F. (38.3° C.) or below 96.8° F. (36° C.); heart rate higher than 90 beats per minute; and respiratory rate higher than 20 breaths per minute. A sepsis diagnosis can be upgraded to severe sepsis when an individual also exhibits at least one sign or symptom including: significantly decreased urine output; abrupt change in mental status; decreased platelet count; difficulty breathing; abnormal heart pumping function; and abdominal pain. A diagnosis of septic shock can be made when an individual has the signs and symptoms of severe sepsis and an extremely low blood pressure that does not adequately respond to simple fluid replacement as determined by those skilled in the art such as medical professionals.

Thrombomodulin is an endothelial transmembrane protein and its highest concentration in the circulation is detected in the capillary bed or microcirculation. The role of endothelial thrombomodulin recruiting thrombin from the turbulent blood flow and converting it to an anticoagulant enzyme is disrupted under pathological conditions such as sepsis. This leads to scarce activation of protein C, localized coagulation and thrombosis. In sepsis, endothelial cell expression of thrombomodulin is strongly downregulated, causing an impaired activation of protein C that is central in the modulation of coagulation activation and inflammatory processes. In addition, thrombomodulin itself has marked immunomodulatory effects, targeting neutrophil adhesion, complement activation and cytokine generation.

The method can further include administering an antidote to the individual in need thereof. An antidote can be administered to the individual to reduce or block the activity of the thrombin-thrombomodulin fusion protein.

The disclosure will be more fully understood upon consideration of the following non-limiting Examples.

EXAMPLES

Example 1

Preparation of Thrombin-Thrombomodulin Fusion Proteins

In this Example, the preparation of a DNA construct encoding thrombin-linker-thrombomodulin fusion proteins is described.

A plasmid-encoding prethrombin-1 cDNA containing a factor V secretion peptide and a HPC4 purification epitope at the N-terminus served as starting genetic material. Using PCR, cDNA encoding soluble Epidermal Grown Factors or EGF domains of thrombomodulin (known as $TM_{456}$) was fused before the ending codon of the prethrombin 1 sequence. At the junction between prethrombin-1 and $TM_{456}$ different linkers containing repetitive sequences of glycine, serine and alanine residues were introduced. An additional restriction site for ecarin venom cleavage-activation was inserted into the prethrombin-1 cDNA for activation and purification purposes. DNA constructs were verified by DNA sequencing. A total of 7 fusion proteins with linkers spanning 7-69 residues were expressed in mammalian cells and purified to homogeneity.

Example 2

In this Example, kinetic experiments of thrombin-thrombomodulin fusion proteins were performed.

Kinetic experiments were performed to compare the activity of thrombin and the fusion proteins towards procoagulant substrates (fibrinogen and PAR-1) and the anticoagulant substrate protein C. The specificity of cleavage ($k_{cat}/K_m$) for each fusion protein towards each substrate is reported in table 1. When compared with thrombin, the fusion proteins displayed a significant reduction of fibrinogen and PAR-1 cleavage.

TABLE 2

| | PC Activation ($mM^{-1}sec^{-1}$) | PC Activation + TM ($mM^{-1}sec^{-1}$) | Fibrinogen (FpA) ($\mu M^{-1}sec^{-1}$) | PAR-1 ($\mu M^{-1}sec^{-1}$) |
|---|---|---|---|---|
| Thrombin | 0.103 | 220 | 17 | 30 |
| L7 | 1.8 | 7.22 | 0.71 | 1.6 |
| L17 | 6.0 | 32.9 | 1.66 | 2.0 |
| L31 | 85 | 155 | 0.25 | 0.3 |
| L41 | 107 | 175 | 0.61 | 1.1 |
| L55 | 120 | 220 | 1.33 | 2.2 |
| L69 | 73.9 | 175 | 1.3 | 2.2 |
| WE | 1E−5 | 12 | 8.9E−4 | 2.6E−2 |
| L31-WE | 0.69 | 1.27 | 2.3E−4 | 6.3E−4 |

As shown in FIG. 1, the clotting time was also prolonged up to 50 fold (FIG. 1B). On the other hand, even in the absence of exogenous thrombomodulin, protein C activation was retained (FIG. 1A). The best performing fusion proteins had a peptide linker ranging from about 20 amino acid residues to about 50 amino acid residues. Unexpectedly, Short (less than about 20 amino acid residues) and long peptide linkers (exceeding about 50 amino acid residues) impaired optimal docking to exosite-1.

As shown in FIG. 1C, 400 nM of a thrombin-thrombomodulin fusion protein using a WE thrombin domain and a 31 amino acid residue linker had a decreased aPTT ratio protein C deficient (PC Def) plasma as compared to normal plasma.

As demonstrated herein, the thrombin-thrombomodulin fusion proteins of the present disclosure exhibit selective reduction towards procoagulant substrates. Results presented herein demonstrated that fibrinogen and PAR-1 cleavage were compromised by 50000-fold. Unexpectedly, while protein C activation was also reduced, the thrombin-thrombomodulin fusion proteins worked well as anticoagulants and prolonged the aPTT time in a dose-dependent manner.

Example 3

In this Example, pharmacodynamics effects of the thrombin-linker-thrombomodulin fusion proteins are described.

Approval of the Institutional Animal Care and Use Committee will be obtained. The pharmacodynamic effects of the thrombin-linker-thrombomodulin fusion proteins will be studied in a primate model of hemostasis and thrombosis. Baboons will be administered the thrombin-linker-thrombomodulin fusion proteins via high-flow exteriorized arteriovenous shunts. Following administration, bleeding time measurements and blood sampling will be obtained from restrained, conscious seated animals. Anxiety, if noted, will be managed with low-dose ketamine (maximum: 2 mg/kg per hour) with or without diazepam (0.5 mg/kg per hour). All pharmacological agents will be injected into, and blood samples will be collected from, the shunts. Blood sampling will be restricted to less than 2% of the blood volume on any experimental day.

Treatments will be administered by intravenous infusion. The effects of intravenous thrombin-thrombomodulin fusion proteins will be systematically evaluated in and around the reported clinically relevant dose range of interventional indications. Studies with higher doses are expected to increase bleeding risk in the animals. The equiefficacious doses of the fusion proteins will be determined by administering a dosage range of from 2 µg/kg per hour to 2 mg/kg per hour. The test dosage range will be expanded to dosages lower than 2 µg/kg per hour and higher than 2 mg/kg per hour to identify the lowest dosage resulting in the anticoagulant effect and the highest dosage resulting in increased bleeding risk.

The hemostatic safety of the thrombin-thrombomodulin fusion protein administration will be assessed as prolongation of the standard template skin bleeding time in comparison with the pretreatment baseline. The measurements will be performed using an FDA-approved incision device (Surgicutt; International Technidyne, Edison, N.J.). Sequential cuts will be performed as instructed immediately before and approximately 40 minutes after the start of treatments. Any prolongation will be considered to be an antihemostatic effect. Unlike several other bleeding time tests, this test has been shown to be sensitive for the detection of changes in hemostasis during the treatment of patients with antithrombotic or hemostatic products. The test has also been shown to be sensitive to the hemorrhagic effects of virtually all tested antithrombotic agents at antithrombotic doses, including direct thrombin inhibitors, activated protein C preparations, or glycoprotein αIIbβ3 inhibitors under experimental conditions in the baboon. Other safety observations will include hemoglobin and hematocrit measurements, as well as thorough clinical monitoring of the study subjects.

In brief, every animal will receive $^{125}$I-labeled purified baboon fibrinogen and $^{111}$In-tropolone-labeled autologous platelets for quantitative assessment of thrombus formation. Thrombus-forming conduit segments will be deployed into the arteriovenous shunts during the last 60 minutes of anticoagulation. The device will consist of a 0.25-mL volume prosthetic vascular graft (4-mm ID), followed distally by a 20-mm long connector tubing and a 1.27-mL volume 9-mm ID silicone rubber extension segment ("thrombus chamber"). The flow rate will be restricted to 100 mL/min during the experiment. Thrombosis will be quantified as the total amount of deposited fibrin in the thrombus chamber. Inhibition of fibrin deposition in the thrombus chamber will be quantified to establish the equiefficacious doses of the fusion proteins. Real-time assessment of platelet deposition in the thrombus chamber will provide additional information about thrombogenesis. Fibrin and platelet deposition will also be determined in the graft segments.

Blood samples (0.9 mL) will be collected into 0.1 mL 3.2% citrate and 0.1 mL citrate/benzamidine to monitor select coagulation parameters immediately before and several times during thrombogenic device placements. The activated partial thromboplastin time (APTT) test will be used for monitoring the systemic effect of each injected fusion protein. The APTT will be determined in citrated plasma using a commercial point-of-care test (Rapid Point Coag; Bayer Diagnostics, Tarrytown, N.Y.) between 5 and 7 minutes after blood drawing. To investigate the association between circulating APC levels and hemostatic safety or antithrombotic efficacy of the fusion proteins, APC levels will also be determined in treated animals using frozen citrate/benzamidine plasma samples. The protein C zymogen levels will be measured as described to assess potential substrate depletion during treatment. Additional EDTA-anticoagulated samples will be used for thrombus size calculations as described and for monitoring potential adverse events, such as platelet and fibrinogen consumption, or bleeding.

It is expected that the fusion proteins will be antithrombotic and prolong the template bleeding time.

What is claimed is:

1. A thrombin-thrombomodulin fusion protein comprising a thrombin domain selected from the group consisting of a full-length thrombin polypeptide, a preprothrombin polypeptide, a prothrombin polypeptide, a prethrombin 1 polypeptide, a prethrombin 2 polypeptide, a thrombin A chain, a thrombin B chain, and combinations thereof, wherein the full-length thrombin polypeptide is set forth in SEQ ID NO:3 or SEQ ID NO:5; a linker selected from the group consisting of a peptide linker, a chemical linker, and combinations thereof; and a thrombomodulin domain selected from the group consisting of a full-length thrombomodulin protein and a thrombomodulin epidermal growth factor-like domain 456 (TM456), wherein the TM456 is set forth in SEQ ID NO:7 or SEQ ID NO:9.

2. The fusion protein of claim 1, wherein the linker domain ranges from about 20 amino acid residues to about 50 amino acid residues.

3. The fusion protein of claim 1, wherein the thrombin domain further comprises one of a thrombin cleavage site and an ecarin cleavage site.

4. The fusion protein of claim 1, wherein the thrombomodulin domain comprises a full-length thrombomodulin protein.

5. The fusion protein of claim 1, wherein the thrombomodulin domain comprises a thrombomodulin epidermal growth factor-like domain 456 (TM456).

* * * * *

SEQUENCE LISTING

<160> NUMBER OF SEQ ID NOS: 25

<210> SEQ ID NO 1
<211> LENGTH: 622
<212> TYPE: PRT
<213> ORGANISM: Homo sapiens

<400> SEQUENCE: 1

Met Ala His Val Arg Gly Leu Gln Leu Pro Gly Cys Leu Ala Leu Ala

```
1               5                   10                  15
Ala Leu Cys Ser Leu Val His Ser Gln His Val Phe Leu Ala Pro Gln
            20                  25                  30
Gln Ala Arg Ser Leu Leu Gln Arg Val Arg Arg Ala Asn Thr Phe Leu
            35                  40                  45
Glu Glu Val Arg Lys Gly Asn Leu Glu Arg Glu Cys Val Glu Glu Thr
50                  55                  60
Cys Ser Tyr Glu Glu Ala Phe Glu Ala Leu Glu Ser Ser Thr Ala Thr
65                  70                  75                  80
Asp Val Phe Trp Ala Lys Tyr Thr Ala Cys Glu Thr Ala Arg Thr Pro
            85                  90                  95
Arg Asp Lys Leu Ala Ala Cys Leu Glu Gly Asn Cys Ala Glu Gly Leu
            100                 105                 110
Gly Thr Asn Tyr Arg Gly His Val Asn Ile Thr Arg Ser Gly Ile Glu
            115                 120                 125
Cys Gln Leu Trp Arg Ser Arg Tyr Pro His Lys Pro Glu Ile Asn Ser
            130                 135                 140
Thr Thr His Pro Gly Ala Asp Leu Gln Glu Asn Phe Cys Arg Asn Pro
145                 150                 155                 160
Asp Ser Ser Thr Thr Gly Pro Trp Cys Tyr Thr Thr Asp Pro Thr Val
            165                 170                 175
Arg Arg Gln Glu Cys Ser Ile Pro Val Cys Gly Gln Asp Gln Val Thr
            180                 185                 190
Val Ala Met Thr Pro Arg Ser Glu Gly Ser Ser Val Asn Leu Ser Pro
            195                 200                 205
Pro Leu Glu Gln Cys Val Pro Asp Arg Gly Gln Gln Tyr Gln Gly Arg
            210                 215                 220
Leu Ala Val Thr Thr His Gly Leu Pro Cys Leu Ala Trp Ala Ser Ala
225                 230                 235                 240
Gln Ala Lys Ala Leu Ser Lys His Gln Asp Phe Asn Ser Ala Val Gln
            245                 250                 255
Leu Val Glu Asn Phe Cys Arg Asn Pro Asp Gly Asp Glu Glu Gly Val
            260                 265                 270
Trp Cys Tyr Val Ala Gly Lys Pro Gly Asp Phe Gly Tyr Cys Asp Leu
            275                 280                 285
Asn Tyr Cys Glu Glu Ala Val Glu Glu Glu Thr Gly Asp Gly Leu Asp
            290                 295                 300
Glu Asp Ser Asp Arg Ala Ile Glu Gly Arg Thr Ala Thr Ser Glu Tyr
305                 310                 315                 320
Gln Thr Phe Phe Asn Pro Arg Thr Phe Gly Ser Gly Glu Ala Asp Cys
            325                 330                 335
Gly Leu Arg Pro Leu Phe Glu Lys Lys Ser Leu Glu Asp Lys Thr Glu
            340                 345                 350
Arg Glu Leu Leu Glu Ser Tyr Ile Asp Gly Arg Ile Val Glu Gly Ser
            355                 360                 365
Asp Ala Glu Ile Gly Met Ser Pro Trp Gln Val Met Leu Phe Arg Lys
            370                 375                 380
Ser Pro Gln Glu Leu Leu Cys Gly Ala Ser Leu Ile Ser Asp Arg Trp
385                 390                 395                 400
Val Leu Thr Ala Ala His Cys Leu Leu Tyr Pro Pro Trp Asp Lys Asn
            405                 410                 415
Phe Thr Glu Asn Asp Leu Leu Val Arg Ile Gly Lys His Ser Arg Thr
            420                 425                 430
```

Arg Tyr Glu Arg Asn Ile Glu Lys Ile Ser Met Leu Glu Lys Ile Tyr
          435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 2
<211> LENGTH: 1389
<212> TYPE: DNA
<213> ORGANISM: Artificial Sequence
<220> FEATURE:
<223> OTHER INFORMATION: Synthetic

<400> SEQUENCE: 2
atgttcctcg cttgccctgg cttctgggtc ctcgtggtcc taggcagcag ctgggcaggc        60
tgggggaacc tagggctga agcagcaaag cttgaagacc aagtagatcc gcggctcatt       120
gatgggaagg tcgacctgtc acctccattg gagcagtgtg tccctgatcg ggggcagcag       180 taccagggc gcctggcggt gaccacacat gggctcccct gcctggcctg gccagcgca        240 caggccaagg ccctgagcaa gcaccaggac ttcaactcag ctgtgcagct ggtggagaac       300
ttctgccgca acccagacgg ggatgaggag ggcgtgtggt gctatgtggc cgggaagcct       360
ggcgactttg gtactgcga cctcaactat tgtgaggagg ccgtggagga ggagacagga       420
gatgggctgg atgaggactc agacagggcc atcgaagggc gtaccgccac cagtgagtac       480
cagactttct tcaatccgag gacctttggc tcgggagagg cagactgtgg gctgcgacct       540
ctgttcgaga agaagtcgct ggaggacaaa accgaaagag agctcctgga atcctacatc       600
gacgggcgca ttgtggaggg ctcggatgca gagatcggca tgtcaccttg gcaggtgatg       660
cttttccgga agagtcccca ggagctgctg tgtggggcca gcctcatcag tgaccgctgg       720
gtcctcaccg ccgcccactg cctcctgtac ccgcccgg acaagaactt caccgagaat       780
gaccttctgg tgcgcattgg caagcactcc cgcaccaggt acgagcgaaa cattgaaaag       840
atatccatgt tggaaaagat ctacatccac cccaggtaca actggcggga gaacctggac       900
cgggacattg ccctgatgaa gctgaagaag cctgttgcct tcagtgacta cattcaccct       960

-continued

```
gtgtgtctgc cgacaggga acggcagcc agcttgctcc aggctggata caagggggcgg    1020 gtgacaggct ggggcaacct gaaggagacg tggacagcca acgttggtaa ggggcagccc    1080
agtgtcctgc aggtggtgaa cctgcccatt gtggagcggc cggtctgcaa ggactccacc    1140
cggatccgca tcactgacaa catgttctgt gctggttaca agcctgatga agggaaacga    1200
ggggatgcct gtgaaggtga cagtggggga ccctttgtca tgaagagccc ctttaacaac    1260
cgctggtacc aaatgggcat cgtctcatgg ggtgaaggct gtgaccggga tgggaaatat    1320
ggcttctaca cacacgtgtt ccgcctgaag aagtggatac agaaggtcat tgatcagttt    1380
ggagagtag                                                            1389
```

<210> SEQ ID NO 3
<211> LENGTH: 462
<212> TYPE: PRT
<213> ORGANISM: Artificial Sequence
<220> FEATURE:
<223> OTHER INFORMATION: Synthetic

<400> SEQUENCE: 3

```
Met Phe Leu Ala Cys Pro Gly Phe Trp Val Leu Val Val Leu Gly Ser
1               5                   10                  15

Ser Trp Ala Gly Trp Gly Asn Leu Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asn Pro Arg Thr Phe Gly Ser Gly Glu Ala Asp Cys
                165                 170                 175

Gly Leu Arg Pro Leu Phe Glu Lys Lys Ser Leu Glu Asp Lys Thr Glu
            180                 185                 190

Arg Glu Leu Leu Glu Ser Tyr Ile Asp Gly Arg Ile Val Glu Gly Ser
        195                 200                 205

Asp Ala Glu Ile Gly Met Ser Pro Trp Gln Val Met Leu Phe Arg Lys
    210                 215                 220

Ser Pro Gln Glu Leu Leu Cys Gly Ala Ser Leu Ile Ser Asp Arg Trp
225                 230                 235                 240

Val Leu Thr Ala Ala His Cys Leu Leu Tyr Pro Pro Trp Asp Lys Asn
                245                 250                 255

Phe Thr Glu Asn Asp Leu Leu Val Arg Ile Gly Lys His Ser Arg Thr
            260                 265                 270

Arg Tyr Glu Arg Asn Ile Glu Lys Ile Ser Met Leu Glu Lys Ile Tyr
        275                 280                 285
```

Ile His Pro Arg Tyr Asn Trp Arg Glu Asn Leu Asp Arg Asp Ile Ala
290                 295                 300

Leu Met Lys Leu Lys Lys Pro Val Ala Phe Ser Asp Tyr Ile His Pro
305                 310                 315                 320

Val Cys Leu Pro Asp Arg Glu Thr Ala Ala Ser Leu Leu Gln Ala Gly
                325                 330                 335

Tyr Lys Gly Arg Val Thr Gly Trp Gly Asn Leu Lys Glu Thr Trp Thr
                340                 345                 350

Ala Asn Val Gly Lys Gly Gln Pro Ser Val Leu Gln Val Val Asn Leu
                355                 360                 365

Pro Ile Val Glu Arg Pro Val Cys Lys Asp Ser Thr Arg Ile Arg Ile
370                 375                 380

Thr Asp Asn Met Phe Cys Ala Gly Tyr Lys Pro Asp Glu Gly Lys Arg
385                 390                 395                 400

Gly Asp Ala Cys Glu Gly Asp Ser Gly Gly Pro Phe Val Met Lys Ser
                405                 410                 415

Pro Phe Asn Asn Arg Trp Tyr Gln Met Gly Ile Val Ser Trp Gly Glu
                420                 425                 430

Gly Cys Asp Arg Asp Gly Lys Tyr Gly Phe Tyr Thr His Val Phe Arg
                435                 440                 445

Leu Lys Lys Trp Ile Gln Lys Val Ile Asp Gln Phe Gly Glu
450                 455                 460

<210> SEQ ID NO 4
<211> LENGTH: 1389
<212> TYPE: DNA
<213> ORGANISM: Artificial Sequence
<220> FEATURE:
<223> OTHER INFORMATION: Synthetic

<400> SEQUENCE: 4

```
atgttcctcg cttgccctgg cttctgggtc ctcgtggtcc taggcagcag ctgggcaggc        60
tggggggaacc taggggctga agcagcaaag cttgaagacc aagtagatcc gcggctcatt      120
gatgggaagg tcgacctgtc acctccattg gagcagtgtg tccctgatcg ggggcagcag      180
taccagggc gcctggcggt gaccacacat gggctcccct gcctggcctg gccagcgca        240
caggccaagg ccctgagcaa gcaccaggac ttcaactcag ctgtgcagct ggtgagaac        300
ttctgccgca acccagacgg ggatgaggag ggcgtgtggt gctatgtggc cgggaagcct      360
ggcgactttg gtactgcga cctcaactat tgtgaggagg ccgtggagga ggagacagga      420
gatgggctgg atgaggactc agacagggcc atcgaagggc gtaccgccac cagtgagtac      480
cagactttct tcgacgggag gacctttggc tcgggagagg cagactgtgg gctgcgacct      540
ctgttcgaga agaagtcgct ggaggacaaa accgaaagag agctcctgga atcctacatc      600
gacgggcgca ttgtggaggg ctcggatgca gagatcggca tgtcaccttg gcaggtgatg      660
cttttccgga agagtcccca ggagctgctg tgtggggcca gcctcatcag tgaccgctgg      720
gtcctcaccg ccgcccactg cctcctgtac ccgccctggg acaagaactt caccgagaat      780
gaccttctgg tgcgcattgg caagcactcc gcaccaggt acgagcgaaa cattgaaaag      840
atatccatgt tggaaaagat ctacatccac cccaggtaca actggcggga gaacctggac      900
cgggacattg ccctgatgaa gctgaagaag cctgttgcct tcagtgacta cattcaccct      960
gtgtgtctgc ccgacaggga gacgcagcc agcttgctcc aggctggata caaggggcgg     1020
gtgacaggct ggggcaacct gaaggagacg tggacagcca cgttggtaa ggggcagccc    1080
```

```
agtgtcctgc aggtggtgaa cctgcccatt gtggagcggc cggtctgcaa ggactccacc    1140
cggatccgca tcactgacaa catgttctgt gctggttaca agcctgatga agggaaacga    1200
ggggatgcct gtgaaggtga cagtggggga ccctttgtca tgaagagccc ctttaacaac    1260
cgctggtacc aaatgggcat cgtctcatgg ggtgaaggct gtgaccggga tgggaaatat    1320
ggcttctaca cacgtgttt ccgcctgaag aagtggatac agaaggtcat tgatcagttt    1380
ggagagtag                                                           1389
```

<210> SEQ ID NO 5
<211> LENGTH: 462
<212> TYPE: PRT
<213> ORGANISM: Artificial Sequence
<220> FEATURE:
<223> OTHER INFORMATION: Synthetic

<400> SEQUENCE: 5

```
Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Thr Glu
            180                 185                 190

Arg Glu Leu Leu Glu Ser Tyr Ile Asp Gly Arg Ile Val Glu Gly Ser
        195                 200                 205

Asp Ala Glu Ile Gly Met Ser Pro Trp Gln Val Met Leu Phe Arg Lys
    210                 215                 220

Ser Pro Gln Glu Leu Leu Cys Gly Ala Ser Leu Ile Ser Asp Arg Trp
225                 230                 235                 240

Val Leu Thr Ala Ala His Cys Leu Leu Tyr Pro Pro Trp Asp Lys Asn
                245                 250                 255

Phe Thr Glu Asn Asp Leu Leu Val Arg Ile Gly Lys His Ser Arg Thr
            260                 265                 270

Arg Tyr Glu Arg Asn Ile Glu Lys Ile Ser Met Leu Glu Lys Ile Tyr
        275                 280                 285

Ile His Pro Arg Tyr Asn Trp Arg Glu Asn Leu Asp Arg Asp Ile Ala
    290                 295                 300
```

Leu Met Lys Leu Lys Lys Pro Val Ala Phe Ser Asp Tyr Ile His Pro
305                 310                 315                 320

Val Cys Leu Pro Asp Arg Glu Thr Ala Ala Ser Leu Leu Gln Ala Gly
                325                 330                 335

Tyr Lys Gly Arg Val Thr Gly Trp Gly Asn Leu Lys Glu Thr Trp Thr
            340                 345                 350

Ala Asn Val Gly Lys Gly Gln Pro Ser Val Leu Gln Val Val Asn Leu
        355                 360                 365

Pro Ile Val Glu Arg Pro Val Cys Lys Asp Ser Thr Arg Ile Arg Ile
    370                 375                 380

Thr Asp Asn Met Phe Cys Ala Gly Tyr Lys Pro Asp Glu Gly Lys Arg
385                 390                 395                 400

Gly Asp Ala Cys Glu Gly Asp Ser Gly Gly Pro Phe Val Met Lys Ser
                405                 410                 415

Pro Phe Asn Asn Arg Trp Tyr Gln Met Gly Ile Val Ser Trp Gly Glu
            420                 425                 430

Gly Cys Asp Arg Asp Gly Lys Tyr Gly Phe Tyr Thr His Val Phe Arg
        435                 440                 445

Leu Lys Lys Trp Ile Gln Lys Val Ile Asp Gln Phe Gly Glu
    450                 455                 460

<210> SEQ ID NO 6
<211> LENGTH: 360
<212> TYPE: DNA
<213> ORGANISM: Artificial Sequence
<220> FEATURE:
<223> OTHER INFORMATION: Synthetic

<400> SEQUENCE: 6
gtggagcccg tggacccgtg cttcgccaac tgcgagtacc agtgccagcc cctgaaccaa      60
actagctacc tctgcgtctg cgccgagggc ttcgcgccca ttccccacga gccgcacagg     120
tgccagatgt tttgcaacca gactgcctgt ccagccgact gcgaccccaa cacccaggct     180
agctgtgagt gccctgaagg ctacatcctg gacgacggtt tcatctgcac ggacatcgac     240
gagtgcgaaa acggcggctt ctgctccggg gtgtgccaca acctccccgg taccttcgag     300
tgcatctgcg ggcccgactc ggcccttgcc cgccacattg caccgactg tgactccggc     360

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Val Glu Pro Val Asp Pro Cys Phe Ala Asn Cys Glu Tyr Gln Cys Gln
1               5                   10                  15

Pro Leu Asn Gln Thr Ser Tyr Leu Cys Val Cys Ala Glu Gly Phe Ala
            20                  25                  30

Pro Ile Pro His Glu Pro His Arg Cys Gln Met Phe Cys Asn Gln Thr
        35                  40                  45

Ala Cys Pro Ala Asp Cys Asp Pro Asn Thr Gln Ala Ser Cys Glu Cys
    50                  55                  60

Pro Glu Gly Tyr Ile Leu Asp Asp Gly Phe Ile Cys Thr Asp Ile Asp
65                  70                  75                  80

Glu Cys Glu Asn Gly Gly Phe Cys Ser Gly Val Cys His Asn Leu Pro

```
                        85                  90                  95
Gly Thr Phe Glu Cys Ile Cys Gly Pro Asp Ser Ala Leu Ala Arg His
                100                 105                 110
Ile Gly Thr Asp Cys Asp Ser Gly
        115                 120

<210> SEQ ID NO 8
<211> LENGTH: 363
<212> TYPE: DNA
<213> ORGANISM: Artificial Sequence
<220> FEATURE:
<223> OTHER INFORMATION: Synthetic

<400> SEQUENCE: 8
gtggagcccg tggacccgtg cttcagagcc aactgcgagt accagtgcca gcccctgaac    60
caaactagct acctctgcgt ctgcgccgag ggcttcgcgc ccattcccca cgagccgcac   120
aggtgccaga tgttttgcaa ccagactgcc tgtccagccg actgcgaccc caacacccag   180
gctagctgtg agtgccctga aggctacatc ctggacgacg gtttcatctg cacggacatc   240
gacgagtgcg aaaacggcgg cttctgctcc ggggtgtgcc acaacctccc cggtaccttc   300
gagtgcatct gcgggcccga ctcggccctt gcccgccaca ttggcaccga ctgtgactcc   360
ggc                                                                 363

<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Val Glu Pro Val Asp Pro Cys Phe Arg Ala Asn Cys Glu Tyr Gln Cys
1               5                   10                  15
Gln Pro Leu Asn Gln Thr Ser Tyr Leu Cys Val Cys Ala Glu Gly Phe
            20                  25                  30
Ala Pro Ile Pro His Glu Pro His Arg Cys Gln Met Phe Cys Asn Gln
        35                  40                  45
Thr Ala Cys Pro Ala Asp Cys Asp Pro Asn Thr Gln Ala Ser Cys Glu
    50                  55                  60
Cys Pro Glu Gly Tyr Ile Leu Asp Asp Gly Phe Ile Cys Thr Asp Ile
65                  70                  75                  80
Asp Glu Cys Glu Asn Gly Gly Phe Cys Ser Gly Val Cys His Asn Leu
                85                  90                  95
Pro Gly Thr Phe Glu Cys Ile Cys Gly Pro Asp Ser Ala Leu Ala Arg
                100                 105                 110
His Ile Gly Thr Asp Cys Asp Ser Gly
        115                 120

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gly Gly Gly Gly Gly Gly Gly
1               5
```

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Gly Gly Gly Ser Ser Ser Ala Gly Gly Gly Ser Ser Ser Gly Gly Gly
1               5                   10                  15

Gly

<210> SEQ ID NO 12
<211> LENGTH: 31
<212> TYPE: PRT
<213> ORGANISM: Artificial Sequence
<220> FEATURE:
<223> OTHER INFORMATION: Synthetic

<400> SEQUENCE: 12

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly
            20                  25                  30

<210> SEQ ID NO 13
<211> LENGTH: 41
<212> TYPE: PRT
<213> ORGANISM: Artificial Sequence
<220> FEATURE:
<223> OTHER INFORMATION: Synthetic

<400> SEQUENCE: 13

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly Ala
            20                  25                  30

Ser Ser Ser Gly Ser Ala Gly Ser Ser
        35                  40

<210> SEQ ID NO 14
<211> LENGTH: 55
<212> TYPE: PRT
<213> ORGANISM: Artificial Sequence
<220> FEATURE:
<223> OTHER INFORMATION: Synthetic

<400> SEQUENCE: 14

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly Ala
            20                  25                  30

Ser Ser Ser Gly Ser Ala Gly Ser Ser Gly Gly Gly Gly Ala Ser Ser
        35                  40                  45

Ser Gly Ser Ala Gly Ser Ser
    50                  55

<210> SEQ ID NO 15
<211> LENGTH: 69
<212> TYPE: PRT
<213> ORGANISM: Artificial Sequence
<220> FEATURE:
<223> OTHER INFORMATION: Synthetic

<400> SEQUENCE: 15

Gly Gly Gly Ser Ser Ala Gly Gly Gly Ser Ser Gly Gly Gly
1               5                   10                  15

Gly Ser Ser Ser Ala Gly Gly Gly Ser Ser Ser Gly Gly Gly Ser
            20                  25                  30

Ser Ser Ala Gly Gly Gly Ser Ser Ser Gly Gly Gly Ser Ser Ser
        35                  40                  45

Ala Gly Gly Gly Ser Ser Ser Gly Gly Gly Ala Ser Ser Ser Gly
    50                  55                  60

Ser Ala Gly Ser Ser
65

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

Leu Glu Asp Gln Val Asp Pro Arg Leu Ile Asp Gly Lys
1               5                   10

<210> SEQ ID NO 17
<211> LENGTH: 1845
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| atgttcctcg | cttgccctgg | cttctgggtc | ctcgtggtcc | taggcagcag | ctgggcaggc | 60 |
| tgggggaacc | tagggctga | agcagcaaag | cttgaagacc | aagtagatcc | gcggctcatt | 120 |
| gatgggaagg | tcgacctgtc | acctccattg | gagcagtgtg | tccctgatcg | ggggcagcag | 180 |
| taccagggc | gcctggcggt | gaccacacat | gggctcccct | gcctggcctg | gccagcgca | 240 |
| caggccaagg | ccctgagcaa | gcaccaggac | ttcaactcag | ctgtgcagct | ggtggagaac | 300 |
| ttctgccgca | acccagacgg | ggatgaggag | ggcgtgtggt | gctatgtggc | cgggaagcct | 360 |
| ggcgactttg | ggtactgcga | cctcaactat | tgtgaggagg | ccgtgaggga | ggagacagga | 420 |
| gatgggctgg | atgaggactc | agacagggcc | atcgaagggc | gtaccgccac | cagtgagtac | 480 |
| cagactttct | tcgacgggag | gacctttggc | tcgggagagg | cagactgtgg | gctgcgacct | 540 |
| ctgttcgaga | agaagtcgct | ggaggacaaa | accgaaagag | agctcctgga | atcctacatc | 600 |
| gacgggcgca | ttgtgggagg | ctcggatgca | gagatcggca | tgtcaccttg | gcaggtgatg | 660 |
| cttttccgga | agagtcccca | ggagctgctg | tgtggggcca | gcctcatcag | tgaccgctgg | 720 |
| gtcctcaccg | ccgcccactg | cctcctgtac | ccgccctggg | acaagaactt | caccgagaat | 780 |
| gaccttctgg | tgcgcattgg | caagcactcc | cgcaccaggt | acgagcgaaa | cattgaaaag | 840 |
| atatccatgt | tggaaaagat | ctacatccac | cccaggtaca | actggcggga | gaacctggac | 900 |
| cgggacattg | ccctgatgaa | gctgaagaag | cctgttgcct | tcagtgacta | cattcaccct | 960 |
| gtgtgtctgc | ccgacaggga | gacggcagcc | agcttgctcc | aggctggata | caagggcggg | 1020 |
| gtgacaggct | ggggcaacct | gaaggagacg | tggacagcca | acgttggtaa | ggggcagccc | 1080 |
| agtgtcctgc | aggtggtgaa | cctgcccatt | gtggagcggc | cggtctgcaa | ggactccacc | 1140 |

```
cggatccgca tcactgacaa catgttctgt gctggttaca agcctgatga agggaaacga   1200
ggggatgcct gtgaaggtga cagtgggggga ccctttgtca tgaagagccc ctttaacaac   1260
cgctggtacc aaatgggcat cgtctcatgg ggtgaaggct gtgaccggga tgggaaatat   1320
ggcttctaca cacacgtgtt ccgcctgaag aagtggatac agaaggtcat tgatcagttt   1380
ggagagggag gtggatcttc ttctgccggt ggtggttcat cttctggtgg aggtggatct   1440
tcttctgccg gtggtggttc atcttctggt ggaggtggag tggagcccgt ggacccgtgc   1500
ttcagagcca actgcgagta ccagtgccag cccctgaacc aaactagcta cctctgcgtc   1560
tgcgccgagg gcttcgcgcc cattccccac gagccgcaca ggtgccagat gttttgcaac   1620
cagactgcct gtccagccga ctgcgacccc aacacccagg ctagctgtga gtgccctgaa   1680
ggctacatcc tggacgacgg tttcatctgc acggacatcg acgagtgcga aaacggcggc   1740
ttctgctccg gggtgtgcca acctccccc ggtaccttcg agtgcatctg cgggcccgac   1800
tcggcccttg cccgccacat tggcaccgac tgtgactccg gctaa                   1845
```

<210> SEQ ID NO 18
<211> LENGTH: 611
<212> TYPE: PRT
<213> ORGANISM: Artificial Sequence
<220> FEATURE:
<223> OTHER INFORMATION: Synthetic

<400> SEQUENCE: 18

```
Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Glu
                20                  25                  30

Asp Gln Val Asp Pro Arg Leu Ile Asp Gly Lys Val Asp Leu Ser Pro
            35                  40                  45

Pro Leu Glu Gln Cys Val Pro Asp Arg Gly Gln Gln Tyr Gln Gly Arg
        50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Glu Arg
            180                 185                 190

Glu Leu Leu Glu Ser Tyr Ile Asp Gly Arg Ile Val Glu Gly Ser Asp
        195                 200                 205

Ala Glu Ile Gly Met Ser Pro Trp Gln Val Met Leu Phe Arg Lys Ser
    210                 215                 220

Pro Gln Glu Leu Leu Cys Gly Ala Ser Leu Ile Ser Asp Arg Trp Val
225                 230                 235                 240
```

Leu Thr Ala Ala His Cys Leu Leu Tyr Pro Pro Trp Asp Lys Asn Phe
                245                 250                 255

Thr Glu Asn Asp Leu Leu Val Arg Ile Gly Lys His Ser Arg Thr Arg
        260                 265                 270

Tyr Glu Arg Asn Ile Glu Lys Ile Ser Met Leu Glu Lys Ile Tyr Ile
    275                 280                 285

His Pro Arg Tyr Asn Trp Arg Glu Asn Leu Asp Arg Asp Ile Ala Leu
290                 295                 300

Met Lys Leu Lys Lys Pro Val Ala Phe Ser Asp Tyr Ile His Pro Val
305                 310                 315                 320

Cys Leu Pro Asp Arg Glu Thr Ala Ala Ser Leu Leu Gln Ala Gly Tyr
                325                 330                 335

Lys Gly Arg Val Thr Gly Trp Gly Asn Leu Lys Glu Thr Trp Thr Ala
            340                 345                 350

Asn Val Gly Lys Gly Gln Pro Ser Val Leu Gln Val Asn Leu Pro
        355                 360                 365

Ile Val Glu Arg Pro Val Cys Lys Asp Ser Thr Arg Ile Arg Ile Thr
370                 375                 380

Asp Asn Met Phe Cys Ala Gly Tyr Lys Pro Asp Glu Gly Lys Arg Gly
385                 390                 395                 400

Asp Ala Cys Glu Gly Asp Ser Gly Gly Pro Phe Val Met Lys Ser Pro
            405                 410                 415

Phe Asn Asn Arg Trp Tyr Gln Met Gly Ile Val Ser Trp Gly Glu Gly
                420                 425                 430

Cys Asp Arg Asp Gly Lys Tyr Gly Phe Tyr Thr His Val Phe Arg Leu
            435                 440                 445

Lys Lys Trp Ile Gln Lys Val Ile Asp Gln Phe Gly Gly Gly Ser Ser
450                 455                 460

Ser Ala Gly Gly Gly Ser Ser Ser Gly Gly Gly Ser Ser Ser Ala
465                 470                 475                 480

Gly Gly Gly Ser Ser Ser Gly Gly Gly Val Glu Pro Val Asp Pro
                485                 490                 495

Cys Phe Arg Ala Asn Cys Glu Tyr Gln Cys Gln Pro Leu Asn Gln Thr
            500                 505                 510

Ser Tyr Leu Cys Val Cys Ala Glu Gly Phe Ala Pro Ile Pro His Glu
        515                 520                 525

Pro His Arg Cys Gln Met Phe Cys Asn Gln Thr Ala Cys Pro Ala Asp
    530                 535                 540

Cys Asp Pro Asn Thr Gln Ala Ser Cys Glu Cys Pro Glu Gly Tyr Ile
545                 550                 555                 560

Leu Asp Asp Gly Phe Ile Cys Thr Asp Ile Asp Glu Cys Glu Asn Gly
                565                 570                 575

Gly Phe Cys Ser Gly Val Cys His Asn Leu Pro Gly Thr Phe Glu Cys
            580                 585                 590

Ile Cys Gly Pro Asp Ser Ala Leu Ala Arg His Ile Gly Thr Asp Cys
        595                 600                 605

Asp Ser Gly
    610

<210> SEQ ID NO 19
<211> LENGTH: 444
<212> TYPE: PRT
<213> ORGANISM: Artificial Sequence
<220> FEATURE:
<223> OTHER INFORMATION: Synthetic

<400> SEQUENCE: 19

```
Thr Phe Gly Ser Gly Glu Ala Asp Cys Gly Leu Arg Pro Leu Phe Glu
1               5                   10                  15
Lys Lys Ser Leu Glu Asp Lys Glu Arg Glu Leu Leu Glu Ser Tyr Ile
            20                  25                  30
Asp Gly Arg Ile Val Glu Gly Ser Asp Ala Glu Ile Gly Met Ser Pro
        35                  40                  45
Trp Gln Val Met Leu Phe Arg Lys Ser Pro Gln Glu Leu Leu Cys Gly
    50                  55                  60
Ala Ser Leu Ile Ser Asp Arg Trp Val Leu Thr Ala Ala His Cys Leu
65                  70                  75                  80
Leu Tyr Pro Pro Trp Asp Lys Asn Phe Thr Glu Asn Asp Leu Leu Val
                85                  90                  95
Arg Ile Gly Lys His Ser Arg Thr Arg Tyr Glu Arg Asn Ile Glu Lys
            100                 105                 110
Ile Ser Met Leu Glu Lys Ile Tyr Ile His Pro Arg Tyr Asn Trp Arg
        115                 120                 125
Glu Asn Leu Asp Arg Asp Ile Ala Leu Met Lys Leu Lys Lys Pro Val
    130                 135                 140
Ala Phe Ser Asp Tyr Ile His Pro Val Cys Leu Pro Asp Arg Glu Thr
145                 150                 155                 160
Ala Ala Ser Leu Leu Gln Ala Gly Tyr Lys Gly Arg Val Thr Gly Trp
                165                 170                 175
Gly Asn Leu Lys Glu Thr Trp Thr Ala Asn Val Gly Lys Gly Gln Pro
            180                 185                 190
Ser Val Leu Gln Val Val Asn Leu Pro Ile Val Glu Arg Pro Val Cys
        195                 200                 205
Lys Asp Ser Thr Arg Ile Arg Ile Thr Asp Asn Met Phe Cys Ala Gly
210                 215                 220
Tyr Lys Pro Asp Glu Gly Lys Arg Gly Asp Ala Cys Glu Gly Asp Ser
225                 230                 235                 240
Gly Gly Pro Phe Val Met Lys Ser Pro Phe Asn Asn Arg Trp Tyr Gln
                245                 250                 255
Met Gly Ile Val Ser Trp Gly Glu Gly Cys Asp Arg Asp Gly Lys Tyr
            260                 265                 270
Gly Phe Tyr Thr His Val Phe Arg Leu Lys Lys Trp Ile Gln Lys Val
        275                 280                 285
Ile Asp Gln Phe Gly Gly Ser Ser Ala Gly Gly Ser Ser
    290                 295                 300
Ser Gly Gly Gly Ser Ser Ser Ala Gly Gly Ser Ser Ser Gly
305                 310                 315                 320
Gly Gly Val Glu Pro Val Asp Pro Cys Phe Arg Ala Asn Cys Glu
                325                 330                 335
Tyr Gln Cys Gln Pro Leu Asn Gln Thr Ser Tyr Leu Cys Val Cys Ala
            340                 345                 350
Glu Gly Phe Ala Pro Ile Pro His Glu Pro His Arg Cys Gln Met Phe
        355                 360                 365
Cys Asn Gln Thr Ala Cys Pro Ala Asp Cys Asp Pro Asn Thr Gln Ala
    370                 375                 380
Ser Cys Glu Cys Pro Glu Gly Tyr Ile Leu Asp Asp Gly Phe Ile Cys
385                 390                 395                 400
Thr Asp Ile Asp Glu Cys Glu Asn Gly Gly Phe Cys Ser Gly Val Cys
```

```
            405                 410                 415
His Asn Leu Pro Gly Thr Phe Glu Cys Ile Cys Gly Pro Asp Ser Ala
        420                 425                 430

Leu Ala Arg His Ile Gly Thr Asp Cys Asp Ser Gly
        435                 440

<210> SEQ ID NO 20
<211> LENGTH: 1845
<212> TYPE: DNA
<213> ORGANISM: Artificial Sequence
<220> FEATURE:
<223> OTHER INFORMATION: Synthetic

<400> SEQUENCE: 20
atgttcctcg cttgccctgg cttctgggtc ctcgtggtcc taggcagcag ctgggcaggc      60
tgggggaacc tagggctga agcagcaaag cttgaagacc aagtagatcc gcggctcatt     120
gatgggaagg tcgacctgtc acctccattg gagcagtgtg tccctgatcg ggggcagcag     180
taccaggggc gcctggcggt gaccacacat gggctcccct gcctggcctg gccagcgca      240 caggccaagg ccctgagcaa gcaccaggac ttcaactcag ctgtgcagct ggtggagaac     300
ttctgccgca acccagacgg ggatgaggag ggcgtgtggt gctatgtggc cgggaagcct     360
ggcgactttg gtactgcgca cctcaactat tgtgaggagg ccgtgaggga ggagacagga     420
gatgggctga tgaggactca agacaggcc atcgaaggc gtaccgccac cagtgagtac     480
cagactttct tcgacgggag gacctttggc tcgggagagg cagactgtgg gctgcgacct     540
ctgttcgaga agaagtcgct ggaggacaaa accgaaagag agctcctgga atcctacatc     600
gacgggcgca ttgtggaggg ctcggatgca gagatcggca tgtcaccttg gcaggtgatg     660
cttttccgga gagtccccca ggagctgctg tgtggggcca gcctcatcag tgaccgctgg     720
gtcctcaccg ccgcccactg cctcctgtac ccgccctggg acaagaactt caccgagaat     780
gaccttctgg tgcgcattgg caagcactcc cgcaccaggt acgagcgaaa cattgaaaag     840
atatccatgt tggaaaagat ctacatccac cccaggtaca actggcggga aacctggac      900 cgggacattg ccctgatgaa gctgaagaag cctgttgcct tcagtgacta cattcaccct     960
gtgtgtctgc ccgacaggga gacggcagcc agcttgctcc aggctggata caaggggcgg    1020
gtgacaggct ggggcaacct gaaggagacg tggacagcca acgttggtaa ggggcagccc    1080
agtgtcctgc aggtggtgaa cctgcccatt gtggagcggc cggtctgcaa ggactccacc    1140
cggatccgca tcactgacaa catgttctgt gctggttaca gcctgatga agggaaacga    1200 ggggatgcct gtgaaggtga cagtggggga ccctttgtca tgaagagccc ctttaacaac    1260
cgctggtacc aaatgggcat cgtctcagcg ggtgcaggct gtgaccggga tgggaaatat    1320
ggcttctaca cacgtgttt ccgcctgaag aagtggatac agaaggtcat tgatcagttt    1380
ggagagggag gtggatcttc ttctgccggt ggtggttcat cttctggtgg aggtggatct    1440
tcttctgccg gtggtggttc atcttctggt ggaggtggag tggagcccgt ggaccgtgc     1500 ttcagagcca actgcgagta ccagtgccag cccctgaacc aaactagcta cctctgcgtc    1560
tgcgccgagg gcttcgcgcc cattccccac gagccgcaca ggtgccagat gttttgcaac    1620
cagactgcct gtccagccga ctgcgacccc aacacccagg ctagctgtga gtgccctgaa    1680
ggctacatcc tggacgacgg tttcatctgc acggacatcg acgagtgcga aaacggcggc    1740
ttctgctccg gggtgtgcca caacctcccc ggtaccttcg agtgcatctg cgggcccgac    1800
tcggcccttg cccgccacat tggcaccgac tgtgactccg gctaa                    1845
```

<210> SEQ ID NO 21
<211> LENGTH: 611
<212> TYPE: PRT
<213> ORGANISM: Artificial Sequence
<220> FEATURE:
<223> OTHER INFORMATION: Synthetic

<400> SEQUENCE: 21

Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Glu Arg
            180                 185                 190

Glu Leu Leu Glu Ser Tyr Ile Asp Gly Arg Ile Val Glu Gly Ser Asp
        195                 200                 205

Ala Glu Ile Gly Met Ser Pro Trp Gln Val Met Leu Phe Arg Lys Ser
    210                 215                 220

Pro Gln Glu Leu Leu Cys Gly Ala Ser Leu Ile Ser Asp Arg Trp Val
225                 230                 235                 240

Leu Thr Ala Ala His Cys Leu Leu Tyr Pro Pro Trp Asp Lys Asn Phe
                245                 250                 255

Thr Glu Asn Asp Leu Leu Val Arg Ile Gly Lys His Ser Arg Thr Arg
            260                 265                 270

Tyr Glu Arg Asn Ile Glu Lys Ile Ser Met Leu Glu Lys Ile Tyr Ile
        275                 280                 285

His Pro Arg Tyr Asn Trp Arg Glu Asn Leu Asp Arg Asp Ile Ala Leu
    290                 295                 300

Met Lys Leu Lys Lys Pro Val Ala Phe Ser Asp Tyr Ile His Pro Val
305                 310                 315                 320

Cys Leu Pro Asp Arg Glu Thr Ala Ala Ser Leu Leu Gln Ala Gly Tyr
                325                 330                 335

Lys Gly Arg Val Thr Gly Trp Gly Asn Leu Lys Glu Thr Trp Thr Ala
            340                 345                 350

Asn Val Gly Lys Gly Gln Pro Ser Val Leu Gln Val Val Asn Leu Pro
        355                 360                 365

Ile Val Glu Arg Pro Val Cys Lys Asp Ser Thr Arg Ile Arg Ile Thr
    370                 375                 380

Asp Asn Met Phe Cys Ala Gly Tyr Lys Pro Asp Glu Gly Lys Arg Gly
385                 390                 395                 400

Asp Ala Cys Glu Gly Asp Ser Gly Gly Pro Phe Val Met Lys Ser Pro
                405                 410                 415

Phe Asn Asn Arg Trp Tyr Gln Met Gly Ile Val Ser Ala Gly Ala Gly
            420                 425                 430

Cys Asp Arg Asp Gly Lys Tyr Gly Phe Tyr Thr His Val Phe Arg Leu
        435                 440                 445

Lys Lys Trp Ile Gln Lys Val Ile Asp Gln Phe Gly Gly Gly Ser Ser
    450                 455                 460

Ser Ala Gly Gly Gly Ser Ser Gly Gly Gly Ser Ser Ser Ala
465                 470                 475                 480

Gly Gly Gly Ser Ser Gly Gly Gly Val Glu Pro Val Asp Pro
                485                 490                 495

Cys Phe Arg Ala Asn Cys Glu Tyr Gln Cys Gln Pro Leu Asn Gln Thr
            500                 505                 510

Ser Tyr Leu Cys Val Cys Ala Glu Gly Phe Ala Pro Ile Pro His Glu
        515                 520                 525

Pro His Arg Cys Gln Met Phe Cys Asn Gln Thr Ala Cys Pro Ala Asp
    530                 535                 540

Cys Asp Pro Asn Thr Gln Ala Ser Cys Glu Cys Pro Glu Gly Tyr Ile
545                 550                 555                 560

Leu Asp Asp Gly Phe Ile Cys Thr Asp Ile Asp Glu Cys Glu Asn Gly
                565                 570                 575

Gly Phe Cys Ser Gly Val Cys His Asn Leu Pro Gly Thr Phe Glu Cys
            580                 585                 590

Ile Cys Gly Pro Asp Ser Ala Leu Ala Arg His Ile Gly Thr Asp Cys
        595                 600                 605

Asp Ser Gly
    610

<210> SEQ ID NO 22
<211> LENGTH: 444
<212> TYPE: PRT
<213> ORGANISM: Artificial Sequence
<220> FEATURE:
<223> OTHER INFORMATION: Synthetic

<400> SEQUENCE: 22

Thr Phe Gly Ser Gly Glu Ala Asp Cys Gly Leu Arg Pro Leu Phe Glu
1               5                   10                  15

Lys Lys Ser Leu Glu Asp Lys Glu Arg Glu Leu Leu Glu Ser Tyr Ile
            20                  25                  30

Asp Gly Arg Ile Val Glu Gly Ser Asp Ala Glu Ile Gly Met Ser Pro
        35                  40                  45

Trp Gln Val Met Leu Phe Arg Lys Ser Pro Gln Glu Leu Leu Cys Gly
    50                  55                  60

Ala Ser Leu Ile Ser Asp Arg Trp Val Leu Thr Ala Ala His Cys Leu
65                  70                  75                  80

Leu Tyr Pro Pro Trp Asp Lys Asn Phe Thr Glu Asn Asp Leu Leu Val
                85                  90                  95

Arg Ile Gly Lys His Ser Arg Thr Arg Tyr Glu Arg Asn Ile Glu Lys
            100                 105                 110

Ile Ser Met Leu Glu Lys Ile Tyr Ile His Pro Arg Tyr Asn Trp Arg
        115                 120                 125

Glu Asn Leu Asp Arg Asp Ile Ala Leu Met Lys Leu Lys Lys Pro Val
    130                 135                 140

Ala Phe Ser Asp Tyr Ile His Pro Val Cys Leu Pro Asp Arg Glu Thr
145                 150                 155                 160

Ala Ala Ser Leu Leu Gln Ala Gly Tyr Lys Gly Arg Val Thr Gly Trp
                165                 170                 175

Gly Asn Leu Lys Glu Thr Trp Thr Ala Asn Val Gly Lys Gly Gln Pro
                180                 185                 190

Ser Val Leu Gln Val Val Asn Leu Pro Ile Val Glu Arg Pro Val Cys
                195                 200                 205

Lys Asp Ser Thr Arg Ile Arg Ile Thr Asp Asn Met Phe Cys Ala Gly
210                 215                 220

Tyr Lys Pro Asp Glu Gly Lys Arg Gly Asp Ala Cys Glu Gly Asp Ser
225                 230                 235                 240

Gly Gly Pro Phe Val Met Lys Ser Pro Phe Asn Asn Arg Trp Tyr Gln
                245                 250                 255

Met Gly Ile Val Ser Ala Gly Ala Gly Cys Asp Arg Asp Gly Lys Tyr
                260                 265                 270

Gly Phe Tyr Thr His Val Phe Arg Leu Lys Lys Trp Ile Gln Lys Val
                275                 280                 285

Ile Asp Gln Phe Gly Gly Gly Ser Ser Ala Gly Gly Gly Ser Ser
                290                 295                 300

Ser Gly Gly Gly Gly Ser Ser Ala Gly Gly Ser Ser Ser Gly
305                 310                 315                 320

Gly Gly Gly Val Glu Pro Val Asp Pro Cys Phe Arg Ala Asn Cys Glu
                325                 330                 335

Tyr Gln Cys Gln Pro Leu Asn Gln Thr Ser Tyr Leu Cys Val Cys Ala
                340                 345                 350

Glu Gly Phe Ala Pro Ile Pro His Glu Pro His Arg Cys Gln Met Phe
                355                 360                 365

Cys Asn Gln Thr Ala Cys Pro Ala Asp Cys Asp Pro Asn Thr Gln Ala
370                 375                 380

Ser Cys Glu Cys Pro Glu Gly Tyr Ile Leu Asp Asp Gly Phe Ile Cys
385                 390                 395                 400

Thr Asp Ile Asp Glu Cys Glu Asn Gly Gly Phe Cys Ser Gly Val Cys
                405                 410                 415

His Asn Leu Pro Gly Thr Phe Glu Cys Ile Cys Gly Pro Asp Ser Ala
                420                 425                 430

Leu Ala Arg His Ile Gly Thr Asp Cys Asp Ser Gly
                435                 440

<210> SEQ ID NO 23
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: Boc-protected
<222> LOCATION: (1)..(1)
<220> FEATURE:
<221> NAME/KEY: 7-amido-4-methylcoumarin
<222> LOCATION: (4)..(4)

<400> SEQUENCE: 23

```
Leu Ser Thr Arg
1

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Ile Asp Pro Arg Ile Val
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Ile Val Pro Arg Gly Val
1               5
```